(12) United States Patent
Zhu et al.

(10) Patent No.: US 10,695,588 B1
(45) Date of Patent: Jun. 30, 2020

(54) CRANIAL HAIR LOSS TREATMENT USING MICRO-ENERGY ACOUSTIC SHOCK WAVE DEVICES AND METHODS

(71) Applicant: S-Wave Medical Inc., Foster City, CA (US)

(72) Inventors: Da Zhu, Foster City, CA (US); Zhuoyu Chen, Foster City, CA (US)

(73) Assignee: Sonicon Inc., Vancouver (CA)

( * ) Notice: Subject to any disclaimer, the term of this patent is extended or adjusted under 35 U.S.C. 154(b) by 0 days.

(21) Appl. No.: 16/234,429

(22) Filed: Dec. 27, 2018

(51) Int. Cl.
*A61N 7/00* (2006.01)

(52) U.S. Cl.
CPC ........ *A61N 7/00* (2013.01); *A61N 2007/0034* (2013.01); *A61N 2007/0065* (2013.01); *A61N 2007/0078* (2013.01)

(58) Field of Classification Search
CPC .............. A61N 7/00; A61N 2007/0034; A61N 2007/0065; A61N 2007/0078
See application file for complete search history.

(56) References Cited

U.S. PATENT DOCUMENTS

| | | | |
|---|---|---|---|
| 2,559,227 A | 7/1951 | Rieber | |
| 4,539,989 A | 9/1985 | Forssmann et al. | |
| 4,713,572 A * | 12/1987 | Bokowski | G01G 11/08 310/321 |
| 5,119,801 A | 6/1992 | Eizenhoefer et al. | |
| 5,174,280 A | 12/1992 | Gruenwald et al. | |
| 5,224,468 A | 7/1993 | Grunewald et al. | |
| 5,311,095 A * | 5/1994 | Smith | B06B 1/064 310/334 |
| 5,598,051 A * | 1/1997 | Frey | A61B 8/546 310/327 |
| 5,941,838 A | 8/1999 | Eizenhofer | |
| 6,869,407 B2 * | 3/2005 | Ein-Gal | G10K 15/043 600/439 |
| 7,507,213 B2 | 3/2009 | Schultheiss et al. | |
| 7,527,589 B2 | 5/2009 | Squicciarini | |
| 7,601,127 B2 | 10/2009 | Schultheiss et al. | |
| 7,841,995 B2 | 11/2010 | Schultheiss et al. | |
| 7,988,648 B2 | 8/2011 | Warlick et al. | |
| 8,162,859 B2 | 4/2012 | Schultheiss et al. | |
| 8,257,282 B2 | 9/2012 | Uebelacker et al. | |
| 8,292,835 B1 * | 10/2012 | Cimino | A61N 7/02 601/3 |
| 9,381,380 B2 | 7/2016 | Ein-Gal | |
| 9,913,748 B2 | 3/2018 | Spector | |
| 10,441,498 B1 | 10/2019 | Zhu et al. | |
| 10,441,499 B1 | 10/2019 | Zhu et al. | |
| 2005/0010140 A1 * | 1/2005 | Forssmann | A61B 17/22004 601/4 |
| 2006/0100550 A1 * | 5/2006 | Schultheiss | A61B 17/22004 601/2 |
| 2007/0239074 A1 * | 10/2007 | Ein-Gal | A61B 17/2251 601/2 |
| 2007/0239079 A1 * | 10/2007 | Manstein | A61N 7/02 601/2 |

(Continued)

*Primary Examiner* — Joanne M Hoffman
(74) *Attorney, Agent, or Firm* — Morrison & Foerster LLP

(57) ABSTRACT

Devices and methods for treating human cranial hair loss using extracorporeal acoustic shock waves are disclosed. The shock wave device optionally includes a proximal surface, a plurality of shock wave generators disposed on the surface, and a coupling assembly configured to transmit shock waves to a user's scalp.

8 Claims, 10 Drawing Sheets

(56) References Cited

U.S. PATENT DOCUMENTS

| | | |
|---|---|---|
| 2008/0065187 A1 | 3/2008 | Squicciarini |
| 2008/0125835 A1* | 5/2008 | Laurent ............... A61N 5/0617 |
| | | 607/89 |
| 2008/0154157 A1* | 6/2008 | Altshuler ............... A61B 18/26 |
| | | 601/2 |
| 2009/0069678 A1* | 3/2009 | Taniyama ......... A61M 37/0092 |
| | | 600/439 |
| 2011/0230793 A1* | 9/2011 | Larson .................... A61N 7/02 |
| | | 601/2 |
| 2012/0215142 A1 | 8/2012 | Spector |
| 2012/0253240 A1 | 10/2012 | Uebelacker et al. |
| 2015/0073312 A1 | 3/2015 | Ein-gal |
| 2015/0231414 A1 | 8/2015 | Ein-gal |
| 2016/0038770 A1* | 2/2016 | Tyler ....................... A61N 7/02 |
| | | 601/2 |
| 2018/0221688 A1* | 8/2018 | Cioanta ................... A61N 7/00 |
| 2018/0296383 A1 | 10/2018 | Blanche |
| 2019/0151192 A1* | 5/2019 | Yamashita ............... A61N 7/00 |
| 2019/0192377 A1* | 6/2019 | Kaila ................... A61H 23/008 |

\* cited by examiner

500

```
at an extracorporeal shock wave apparatus comprising a housing, a plurality of shock
wave generators disposed on a first surface of the housing, and a coupling assembly      — 502
disposed over and covering the plurality of shock wave generators such that the
plurality of shock wave generators being sandwiched by the housing and the coupling
assembly
```
— 504 the first surface is non-convex has at least one geometric real focal point or focal volume the coupling assembly is configured to transmit the plurality of shock waves to the user's scalp, and the energy of the shock waves are substantially dissipated within the user's scalp and cranium bone before the plurality of shock waves reach the at least one focal point

— 512 the coupling assembly includes a flexible layer sandwiching a couplant with the plurality of shock wave generators

— 506 the coupling assembly further includes a sac configured to contain a volume of liquid the sac is configured to deform in accordance with the volume of liquid contained in the sac

— 516

— 508 the plurality of shock wave generators include a plurality of piezoelectric ceramics tiles configured to momentarily deform in response to receiving an electrical signal

— 510 the plurality of shock wave generators include a plurality of conductive wire segments sandwiched by the housing and a conductive film, the plurality of wire segments configured to conduct an electrical signal, and the conductive film configured to momentarily deform in response to an electromagnetic field generated by the electrical signal in the plurality of conductive wire segments

— 514

The apparatus further includes a control and power supply unit configured to connect to the plurality of shock wave generators, the control and power supply unit configured to control the coupling assembly and a group of the plurality of shock wave generators

— 518

FIG. 5A

CRANIAL HAIR LOSS TREATMENT USING MICRO-ENERGY ACOUSTIC SHOCK WAVE DEVICES AND METHODS

FIELD OF THE INVENTION

This disclosure relates generally to a method for treating human cranial hair loss and, more particularly, for such treatment using an acoustic shock wave generation device.

BACKGROUND

The growth cycle of hair for human comprises three major phases: anagen (growth phase), catagen (recession phase), and telogen (rest phase), as illustrated in FIG. 1A. In the anagen phase, the derma papilla within the hair bulb receives nutrients and oxygen from the strong blood flow and nourishes the hair follicle for hair growth. Inside the bulb surrounding the papilla, hair cells divide rapidly, much faster than the other cells in the human body, resulting in hair growth. The keratin, leftover protein of dead hair cell, are forced upwards as new cells grow beneath them, so that hair length is extended. In normal circumstance, about 90% of hair follicles are in the anagen phase at any given time. The length of the anagen phase is usually about two to seven years, which determines the maximum hair length. After the anagen phase, signals from the scalp skin instruct to cut down the blood supply to the follicles, forming a club hair detached from the papilla, termed the catagen phase. This phase is a transition phase which is usually relatively short and lasts about two weeks. In the final phase, telogen, the club hair rests and ready to be shed. About 10% of hair follicles are in this phase, which lasts around 3 months under a healthy condition. The transition from telogen to anagen happens when quiescent stem cells at the base of the telogen follicle, near the derma papilla, are activated to induce hair cell proliferation.

Dihydrotestosterone (DHT) is a bi-product of a hormone, which can appear in the men's and women's hair follicles. Androgenic Alopecia (male pattern baldness) is caused by the existence of DHT and the hair follicles sensitive to it. The DHT in the papilla disrupts the normal process of nutrients being absorbed by reducing blood flow and suppresses cell proliferation in the follicles, which shortens the anagen phase, prolongs the telogen phase, and shrinks the size of follicles. This triggers the start of the miniaturization until the follicles eventually reach the vellus stage, in which hair is short, thin, very fine, and hardly visible, although still alive with cycles through the three phases, as illustrated in FIG. 1B.

Currently, there are three types of major products/treatments for treating this condition with approval from Food and Drug Association in the United States. (1) Minoxidil is topical medicine applied to the scalp twice a day, for cutting off DHT around the scalp area. However, using this drug, only around ¼ of men and ⅕ of women experience some hair regrowth within 2 to 4 months. Side effects include oiliness, dryness, or irritation of the scalp. It may also cause unwanted facial hair growth for women. Once the drug application is discontinued, the gained hair will be lost with the possibility of losing more hair. (2) Oral finasteride, taken once daily, blocks the formation of DHT. Side effects include diminished libido and sexual dysfunction. The finasteride has little effect in accelerating the hair restoration, but to prevent further hair loss from DHT. Yet, once the intake of drug is discontinued, DHT is formed again and causes hair loss. (3) Low level laser therapy, utilizing visible red light, delivers light energy to the scalp to increases the amount of adenosine triphosphate (ATP) produced by mitochondria, promoting cellular activity for hair growth. This therapy is suitable for men and women who are in the early stage to the hair loss. The efficacy of the product relies on the sufficient number of follicles without significant miniaturization, but has little effect on miniaturized follicles.

Shock waves are propagating pressure pulses in elastic media, such as air, water and human/animal tissue. Acoustic shock waves have been used for various medical purposes as a noninvasive and non-surgical treatment. It has been proven to be effective to treat a variety of medical conditions in various clinical practices and research reports. For example, in urology, high-intensity focused shock waves are used for breaking kidney/bladder/urethra stones into small fragments on the order of several millimeters in diameter (i.e., lithotripsy), so that the small pieces can be transported out of the patient's body through the urethra. In orthopedics, shock waves are used for pain and inflammation relief/curing in joints and healing of bones. In more recent developments, low-intensity shock waves are found to be effective in modulation of various mechanisms, depending on different types of tissues and conditions. These effects include angiogenesis, nerve regeneration, anti-inflammation, and the induction and acceleration of cell proliferation and stem cell recruitment.

Acoustic shock wave generation is often based on three different mechanisms: electrohydraulic, electromagnetic, and piezoelectric. In the electrohydraulic method (see, e.g., U.S. Pat. No. 4,539,989, incorporated herein by reference), a pulse electric discharge between two closely positioned electrodes inside water induces a sudden vaporization of small amount of water nearby. This rapid increase of volume caused by the vaporization creates a pressure pulse in the water, thus generates radial propagating shock waves. In the electromagnetic method (see, e.g., U.S. Pat. No. 5,174,280, incorporated herein by reference), an electric current pulse in a conductor coil results in a pulsed electromagnetic field, which in turn repels a conductive film having certain elastic properties and positioned closely to the coil, thereby generating a momentary (e.g., pulsed) displacement in the conductive film. The momentary displacements in turn generate shock waves with wave fronts parallel to the metal film surface. Alternatively, in the piezoelectric shock wave generation method (see, e.g., U.S. Pat. No. 5,119,801, incorporated herein by reference), electrical voltage pulses are applied to an array of piezoelectric ceramic tiles. The voltage pulses induce volume expansions and contractions of the ceramics with each, thereby generating shock waves with wave fronts parallel to the ceramic surfaces.

SUMMARY OF THE INVENTION

The prior art designs of shock wave generation are well-suited for treating small target (e.g., lithotripsy), but they fail to fulfill the need for treating homogeneously and simultaneously large target areas, such as human scalp, which is needed in many new low-intensity and micro-energy medical applications. There is a need for a device that optimizes generation of a shock wave field that reach a large target area so that a substantial part of a person's scalp, can be treated by the shock wave simultaneously and homogeneously. There is also a need for a specific design of shock wave transducer for treating human scalp with energy that is within an appropriate rage for the effectiveness and adequately low (micro-energy) so that it does not introduce unwanted damage. Importantly, the present disclosure introduces a brand new approach for treating human hair loss, a medical challenge that is far from resolved.

The present disclosures seek to utilize micro-energy shock waves for promoting human hair growth and reverse miniaturization through angiogenesis, blood flow improvement, and stem cell activation for hair follicles. Some aspects of the present disclosure provide a device and method for treating a scalp using generating an acoustic shock wave field. The shock wave device optionally includes a plurality of shock wave generators. In some embodiments, the plurality of shock wave generators optionally include a combination of a conductive thin film and a plurality of conductive wire segments sandwiched by the conductive thin film and the housing, where the conductive thin film and the conductive wire segments are insulated from each other. In some embodiments, the plurality of shock wave generators optionally include a plurality of piezoelectric ceramics disposed on a proximal surface of the housing. In some embodiments, the shock wave device optionally includes a coupling assembly disposed over the plurality of shock wave generators, where the coupling assembly is configured to transmit the shock waves to a user's scalp. In some embodiments, the coupling assembly comprises a deformable polymer (e.g. silicone) pad. In some embodiments, the coupling assembly optionally has a deformable sac configured to hold shock wave transmitting liquid. The volume of the transmitting liquid is optionally increased or decreased as needed so that the coupling assembly can conform to the shape of the scalp.

The various aspects of the present disclosure provide devices and method that can treat a large area of the scalp simultaneously, with appropriate micro-energy density, for an effective, efficient, and consistent treatment avoiding the extensive scanning using directed shock wave sources in prior arts.

BRIEF DESCRIPTION OF THE DRAWINGS

FIGS. 5A-5B illustrate methods of using a shock wave device according to various aspects of the present disclosure.

DETAILED DESCRIPTION OF EMBODIMENTS

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

Figure 1A:
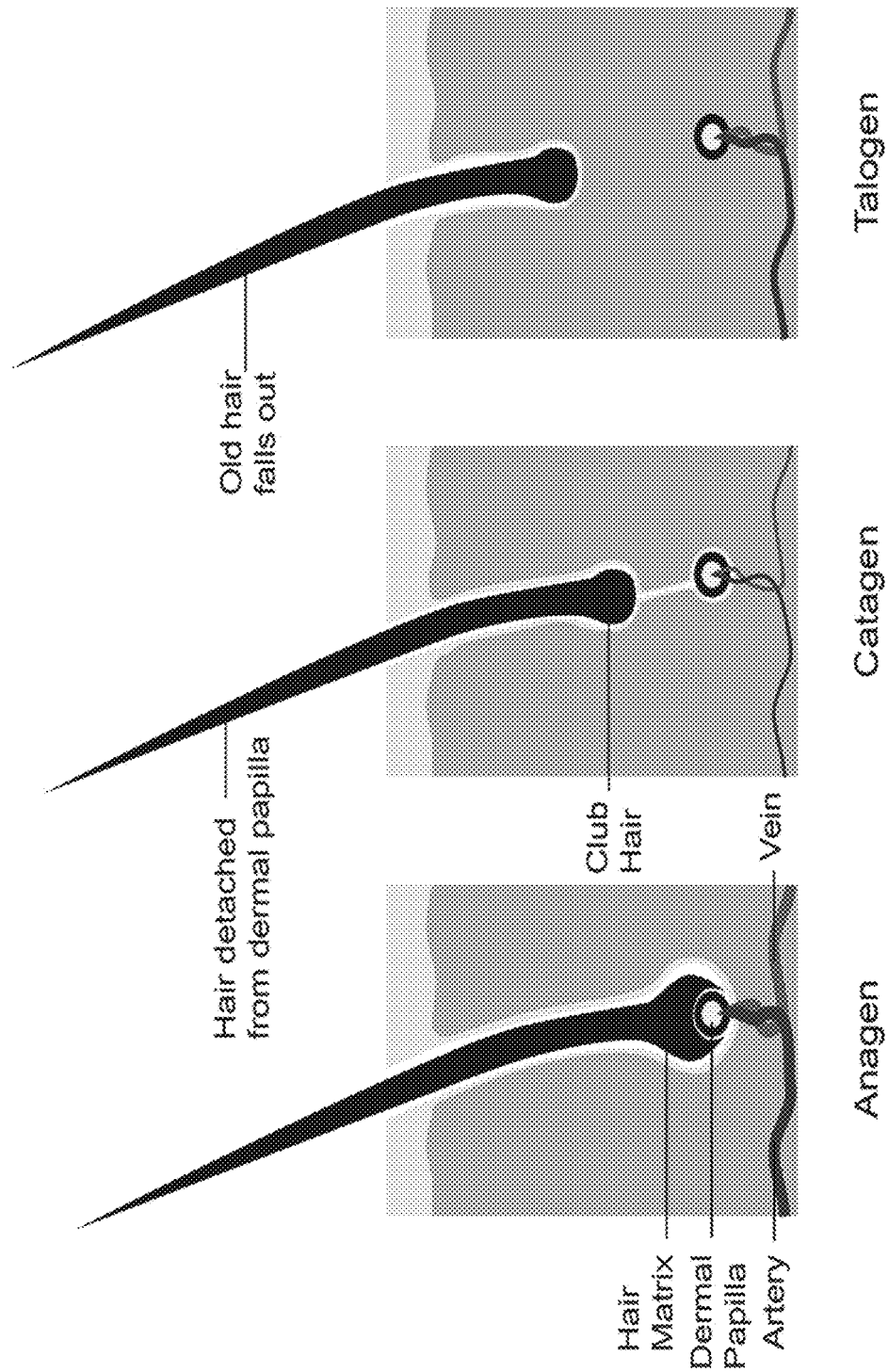
FIG. 1A illustrates the growth cycle of hair for human comprises three major phases: anagen (growth phase), catagen (recession phase), and telogen (rest phase).
Figure 1B:
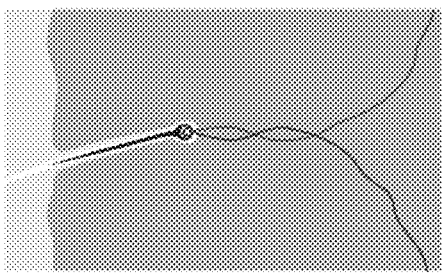
FIG. 1B illustrates the hair miniaturization process.
Figure 1B:
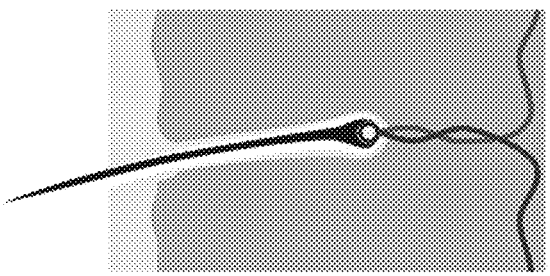
Figure 1B:
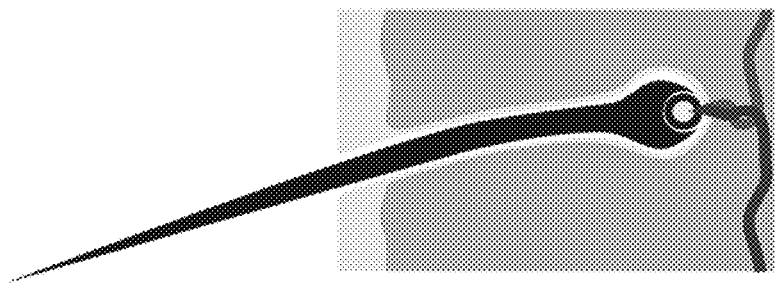
Figure 1C:
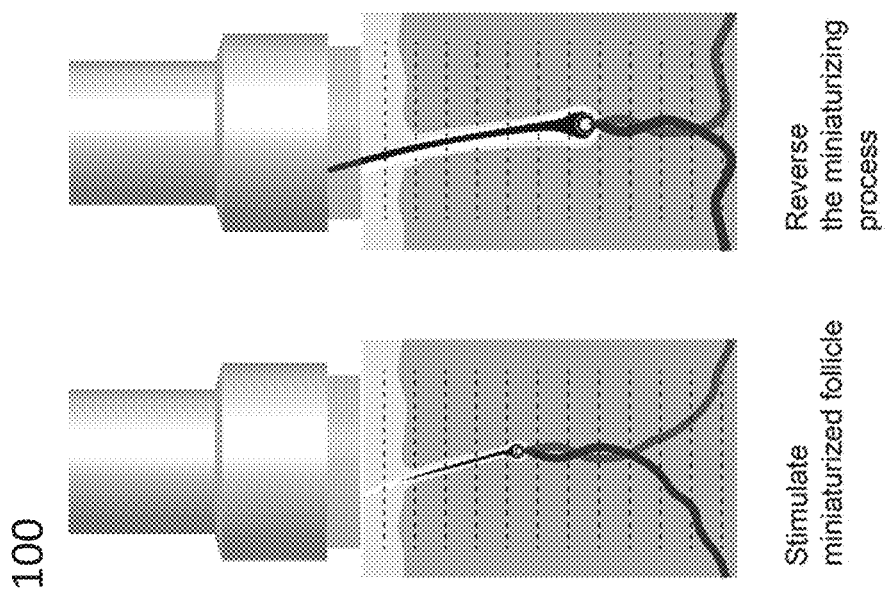
FIG. 1C illustrates an exemplary method to stimulate miniaturized hair follicle and reverse the miniaturizing process according to various aspects in the present disclosure.

FIG. 1C illustrates an exemplary method to stimulate miniaturized hair follicle and reverse the miniaturizing process according to various aspects in the present disclosure. As showing in FIG. 1C, micro-energy shock wave generating device 100 optionally contacts a scalp area that has miniaturized follicles and generates one or more shock wave pressure pulses. The pressure pulses reach the miniaturized follicle as well as the connecting artery and vein, thereby stimulating the miniaturized follicle, artery, and vein in the process. The regenerated artery and vein in turn can improve blood flow to and activate the stem cell for hair follicles, thereby regenerating the follicle and reverse the hair miniaturizing process.

Figure 2B:
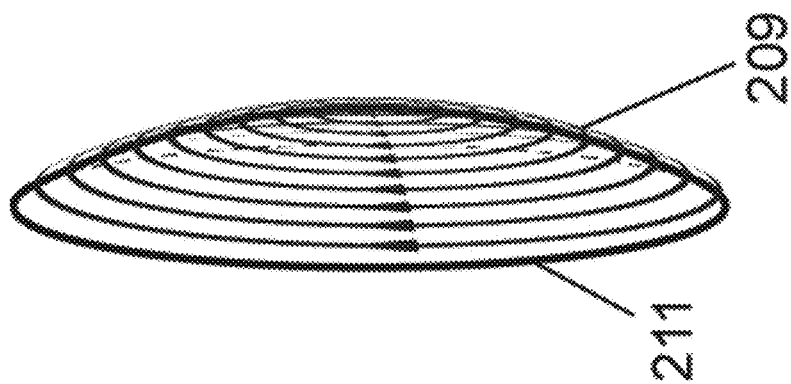
FIGS. 2A-2B illustrate an exemplary shock wave device 200 according to various aspects in the present disclosure.
Figure 2A:
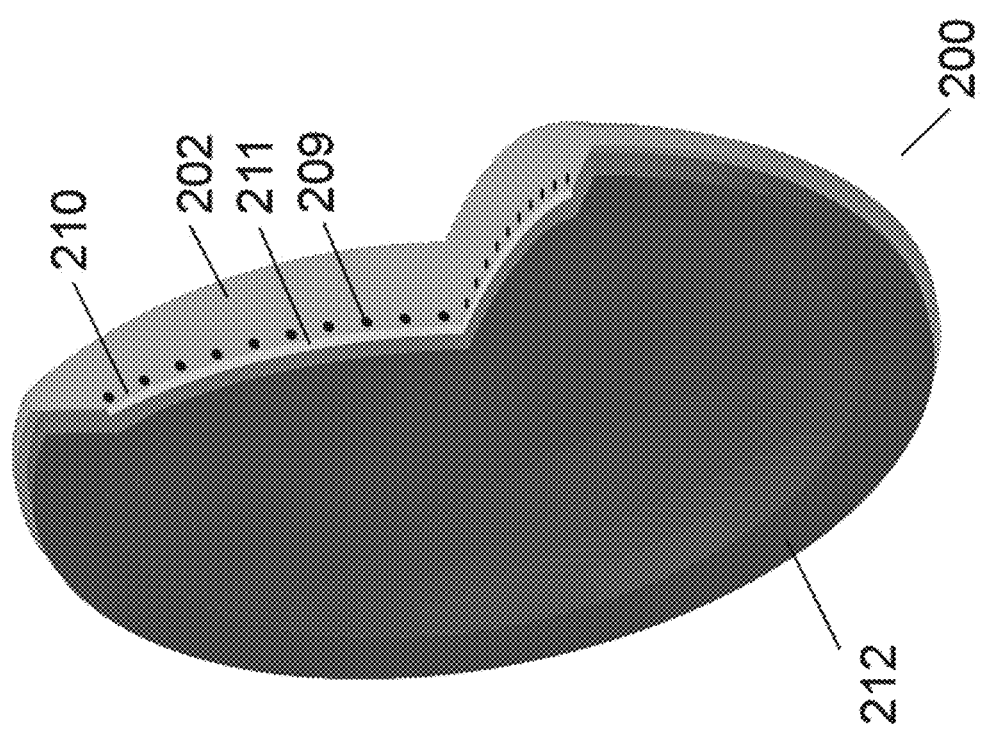

FIGS. 2A-2B illustrate an exemplary shock wave device 200 according to various aspects of the present disclosure. The device 200 includes a housing 202 having a proximal surface 210. In some embodiments, the housing is optionally manufactured using various suitable materials generally known in the art, such as metal or plastic; the housing is optionally manufactured using production processes generally known in the art, such as injection molding, Computer Numerical Control (CNC) subtractive machining, or computerized additive manufacturing (i.e., 3-D Printing). Shock wave device 200 further includes multiple electromagnetic shock wave generators: specifically, multiple turns of a conductive wire coil 209 sandwiched between a conductor film 211 and the housing 202. The multiple electromagnetic shock wave generators (209 and 211) are located on at least a substantial portion of the proximal surface 210 of the housing 202, so that shock waves originate from a substantial area of the proximal surface 210. The proximal surface 210 is optionally flat or concave and has no focal point or at least one geometric real focal point or focal volume defined by the three-dimensional curvature of the proximal surface 210, and the coupling assembly 212 is configured to transmit the plurality of shock waves to the user's scalp.

In some preferred embodiments, as illustrated in FIGS. 2A-2B, the multiple electromagnetic shock wave generators are located throughout substantially all of the proximal surface 210. Each shock wave generator (e.g., the combination of each turn of a conductive wire coil 209 and the conductor film 211) is configured to generate a shock wave: when a pulsed electric current is applied in the coil (e.g., 209, shown in FIG. 2B together with conductive thin film 211 without showing the housing), an electromagnetic field with pulsed energy is generated. Notably, the pulsed electromagnetic field is significantly different from a static magnetic field that could be generated by this coil with a constant flowing electric current. Based on Maxwell's equations, a rapidly changing magnetic field in time would generate electric field, and the generated electric field would also generate magnetic field since it is changing rapidly as well. Therefore, the electromagnetic field generated by the pulsed current in the coil is a complex electromagnetic field which expels the metal thin film to make a sudden elastic displacement. Such displacement results in a pressure pulse and generates shock wave propagating away from the conductive film. Device 200 also includes a coupling assembly 212. In some embodiments, the coupling assembly comprises a flexible polymer (e.g. silicone) layer sandwiching a couplant (e.g. glycerin, or aqueous gel containing polyols and corrosion inhibitor) with the generators. In some embodiments, the coupling assembly optionally has a deformable sac configured to hold shock wave transmitting liquid. The volume of the transmitting liquid is optionally increased or decreased as needed so that the coupling assembly can conform to the shape of the scalp.

Figure 2D:
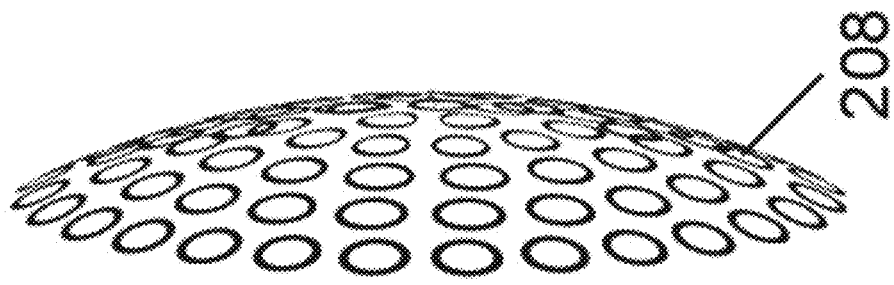
FIGS. 2C-2D illustrate another exemplary shock wave device 200 according to various aspects in the present disclosure.
Figure 2C:
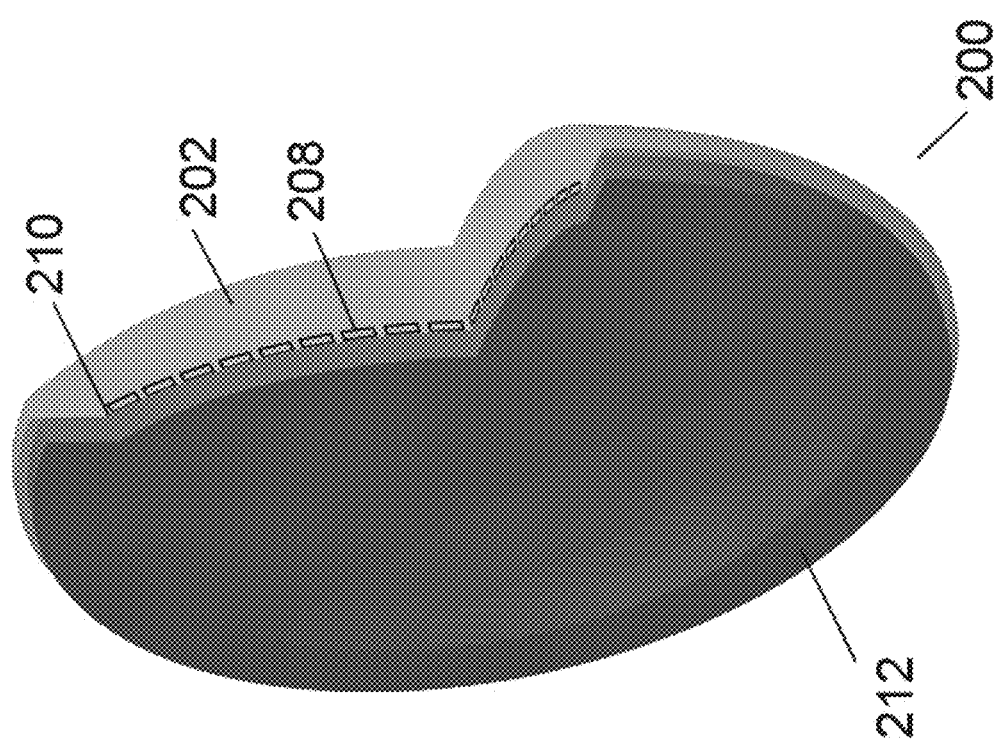

FIGS. 2C-2D illustrate another exemplary shock wave device 200 according to various aspects of the present disclosure. The device 200 includes a housing 202 that has a proximal surface 210. In some embodiments, the housing is optionally manufactured using various suitable materials generally known in the art, such as metal or plastic; the housing is optionally manufactured using production processes generally known in the art, such as injection molding, Computer Numerical Control (CNC) subtractive machining, or computerized additive manufacturing (i.e., 3-D Printing). Shock wave device 200 further includes multiple piezoelectric ceramic tile shock wave generators 208 disposed on the proximal surface 210. The multiple electromagnetic shock wave generators 208 are located on at least a substantial portion of the proximal surface 210, so that shock waves originate from a substantial area of the proximal surface. The proximal surface 210 is optionally flat or concave and has no focal point or at least one geometric real focal point or focal volume defined by the three-dimensional curvature of the proximal surface 210, and the coupling assembly 212 is configured to transmit the plurality of shock waves to the user's scalp. In some preferred embodiments, as illustrated in FIGS. 2C-2D, the multiple piezoelectric shock wave generators are located throughout substantially the entire proximal surface 210. Piezoelectric ceramics tiles 208 (shown round as example) are disposed on the proximal surface 210. A pulsed signal can be applied to any of the piezoelectric tiles and cause sudden expansion and contraction of the tile, thereby generating a pressure pulse. Device 200 also includes a coupling assembly 212.

Figure 3A:
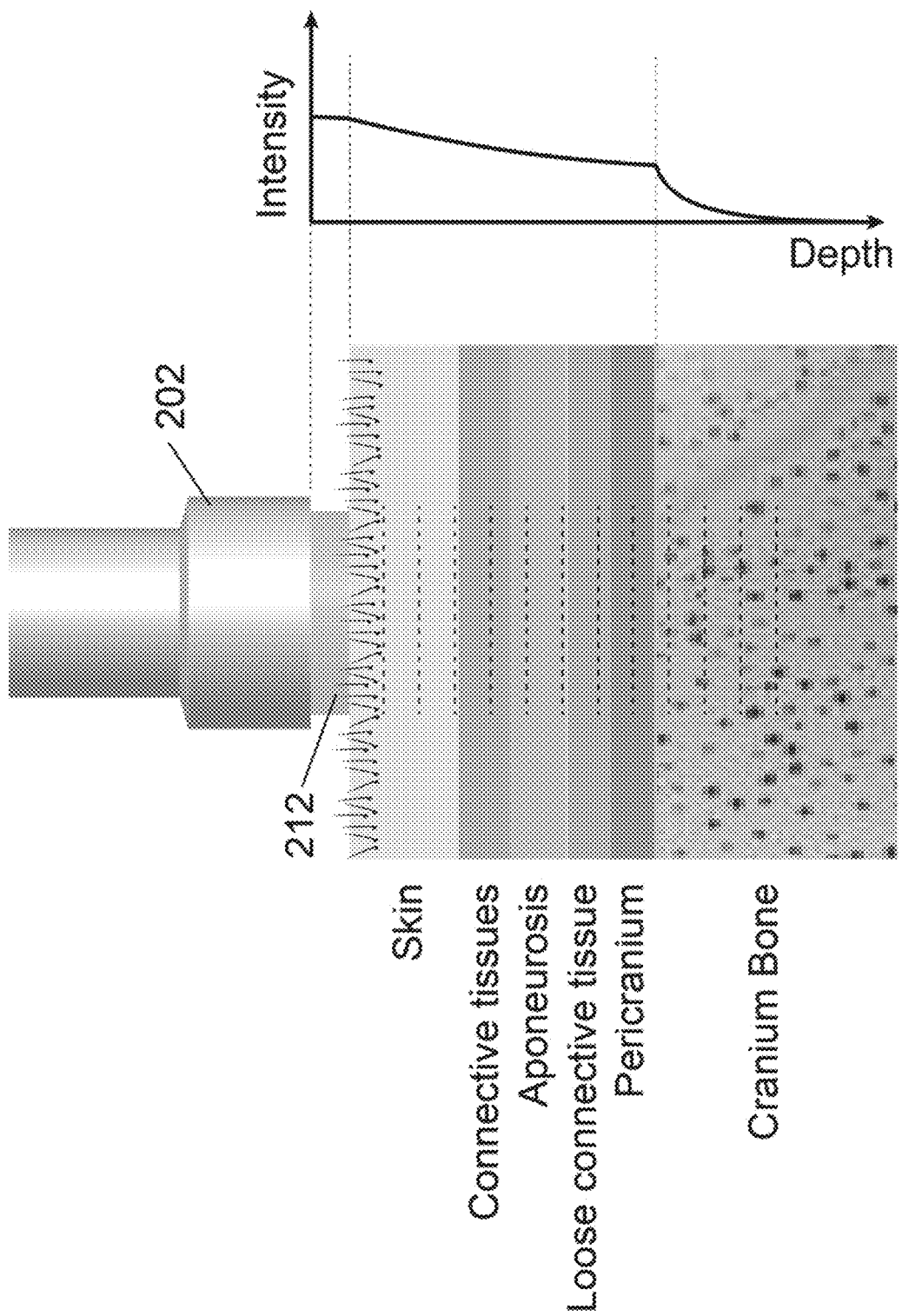
FIGS. 3A-3B illustrate exemplary shock wave intensity gradients generated by exemplary shock wave devices according to various aspects of the present disclosure.
Figure 3B:
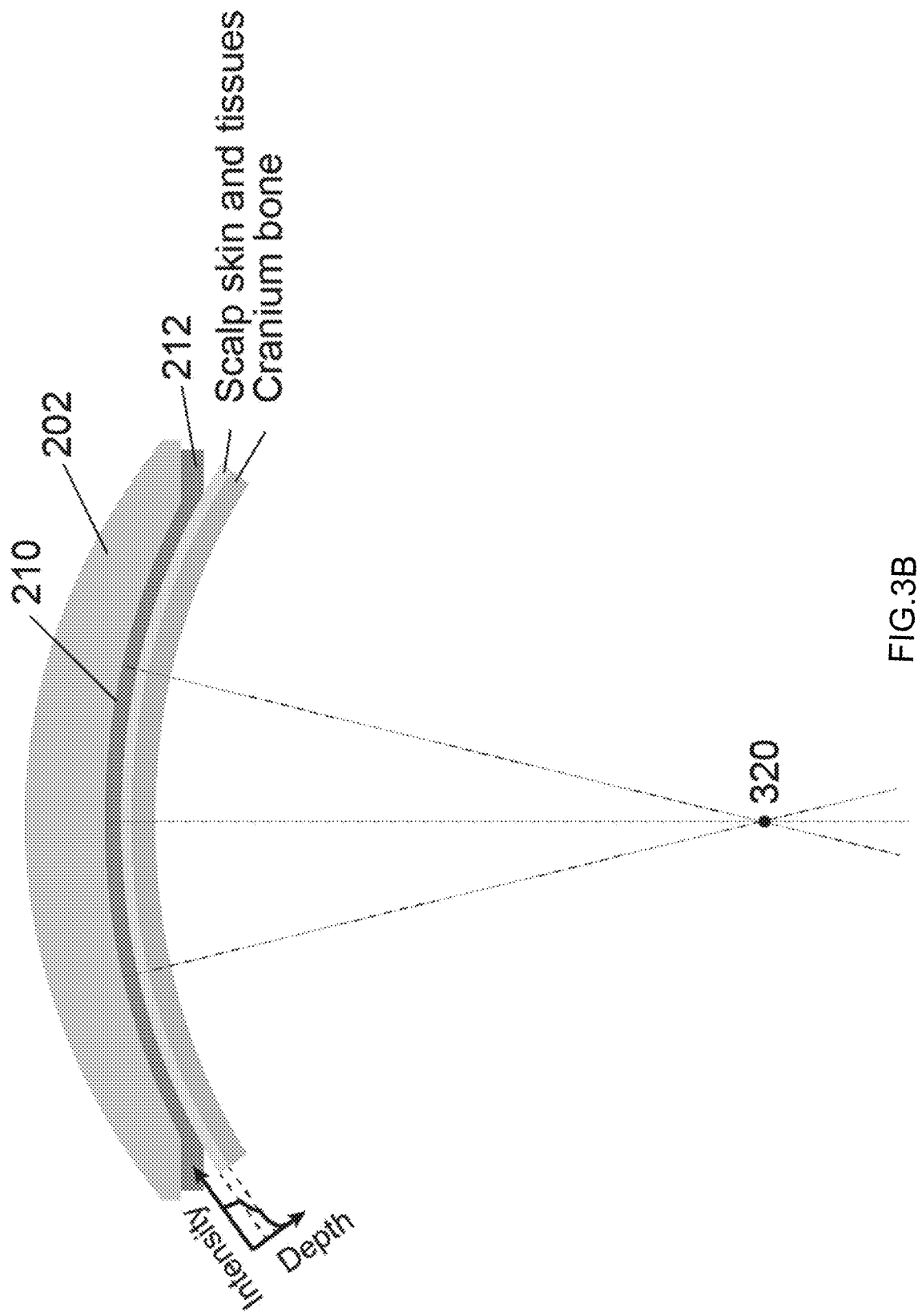

FIGS. 3A-3B illustrate exemplary shock wave energy dissipation and intensity gradient when using the exemplary shock wave devices according to various aspects of the present disclosure. FIG. 3A illustrates an exemplary shock wave intensity as a function of penetrating depth where the shock wave generator device contacts the scalp. The intensity here is defined as shock wave energy density. In some embodiments, part of the shock wave energy generated by the shock wave device is consumed within the treated scalp skin and tissues, while the rest of the energy is substantially dissipated within the cranium bone before the wave reaches the brain. In some embodiments, substantially all energy generated by the shock wave generating device is consumed within the treated scalp skin and tissues before the waves reach the cranium bone. FIG. 3B illustrates another exemplary shock wave energy dissipation and intensity gradient where the shock wave energy generated by the shock wave device (whose housing 202 and coupling assembly 212 are shown) is substantially dissipated within the scalp and the cranium bone before the plurality of shock waves reach the at least one geometric real focal point or focal volume 320 defined by the three-dimensional curvature of the proximal surface 210, on which the plurality of shock wave generators are disposed.

Figure 4:
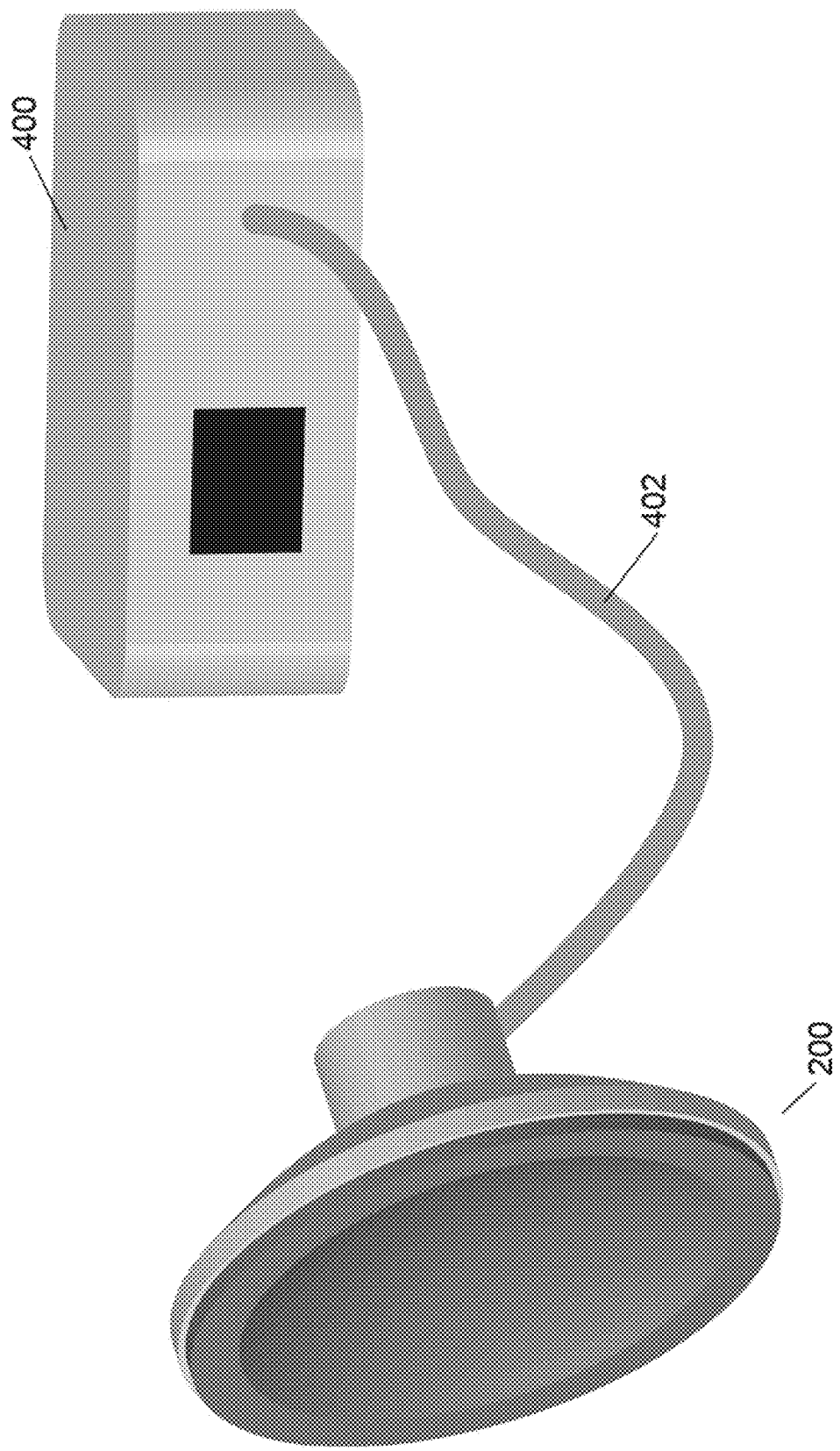
FIG. 4 illustrates an exemplary shock wave device with a control and power supply unit according to various aspects of the present disclosure.

FIG. 4 illustrates an exemplary shock wave device with a control and power supply unit according to various aspects of the present disclosure. The control and power supply unit 400 is configured to connect electrically to the shock wave generators (e.g., 208 or 209 and 211) via a connection line 402 in order to provide a pulsed electrical signal (e.g., an pulsed voltage or a pulsed current) to the shock wave generators. In some embodiments, the control and power supply unit 400 optionally controls the shock wave generators by sending multiple control signals, where each control signal controls a subset of the shock wave generators. In some embodiments, the control and power supply unit optionally includes one or more user-selectable settings that adjust the intensity of shock wave pressure pulses produced by a group of the shock wave generators by, for example, adjusting the pulse amplitude, pulse width, pulse repetition rate, or pulse delay (e.g., phase) of the pulse voltage signal or the pulse current signal.

The control and power supply unit 400 optionally controls the inflation and deflation of the deformable sac 218 in the coupling assembly 212 by filling the deformable sac with shock wave transmission fluid or draining shock wave transmission fluid from the deformable sac via the connection line 402. In some embodiments, the control and power supply unit optionally includes one or more user-selectable settings that adjust the amount of shock wave transmission fluids in the sac. In some embodiments, the control and power supply unit optionally receives an electrical signal corresponding to a measured pressure value from the coupling unit and, in accordance with the measure pressure, stops filling the sac with shock wave transmission liquid.

Various aspects of the present disclosure include an extracorporeal shock wave apparatus (e.g., 200). In some embodiments, the apparatus includes a housing (e.g., 202) with a first surface (e.g., proximal surface 210). In some embodiments, the apparatus optionally includes a plurality of shock wave generators (e.g., 208) disposed on a first surface (e.g., proximal surface 210) of the housing (e.g., the side facing the scalp), each shock wave generator configured to generate a shock wave propagating toward the scalp. In some embodiments, the plurality of shock wave generators are placed uniformly; that is, each of the plurality of shock wave generators is optionally separated by the same distance from another shock wave generator. In some embodiments, the apparatus includes a coupling assembly (e.g., 212) disposed over and covering the plurality of shock wave generators (e.g., 208) thereby sandwiching the plurality of shock wave generators between the first surface (e.g., proximal surface 210) and the coupling assembly (e.g., 212), the coupling assembly configured to contact an area of a user's scalp and to transmit the plurality of shock waves to the user's scalp. In some embodiments, each generated shock wave has a corresponding intensity. In some embodiments, the corresponding intensity is configured to cause the shock wave to dissipate in the user's scalp.

In some embodiments, the first surface (e.g., proximal surface 210) is not convex and has at least one geometric real focal point or focal volume defined by the geometry of the first surface. In some embodiments, the coupling assembly (e.g., 212) is configured to transmit the plurality of shock waves to the user's scalp before the plurality of shock waves reach the at least one geometric focal point or focal volume.

In some embodiments, the apparatus optionally includes a coupling assembly (e.g., 212) that is disposed over and covering the plurality of shock wave generators (e.g., 208) such that the plurality of shock wave generators are sandwiched by the first surface of the housing (e.g., proximal surface 210) and the coupling assembly. In some embodiments the coupling assembly is optionally detachable, that is, the coupling assembly can be repeatedly removed from and re-attached, covering the plurality of shock wave generators disposed on the inside surface of the housing. In some embodiments, the coupling assembly is optionally configured to transmit the plurality of shock waves to the user's scalp. In some embodiments, the coupling assembly optionally includes a medium that transmits shock wave pressure pulses with less intensity decay than air.

In some embodiments, the plurality of shock wave generators optionally includes a plurality of piezoelectric ceramic tiles (e.g., 208) disposed on the proximal surface of the housing. In some embodiments, the piezo electric ceramic tiles are optionally round, oval, hexagonal, rectangular, square, or other shapes generally known in the art In some embodiments, the plurality of piezoelectric ceramic tiles are optionally connected to the power supply and control unit using one or more electrical connection devices such as wires, flexible printed circuits, and embedded printed metal traces, as well as other electrical connection devices generally known in the art. In some embodiments, one or more holes are optionally embedded in the housing in order to pass electrical connection from outside the housing to the shock wave generators.

In some embodiments, the plurality of shock wave generators optionally includes a plurality of conductive wire segments (e.g., 209) sandwiched by (e.g., fitting snugly between) the housing and a conductive film (e.g., 211). In some embodiments, the plurality of conductive wire segments (e.g., 209) are electrically insulated from the conductive film (e.g. 211). The plurality of wire segments are optionally configured to transmit an electrical signal, and the conductive film (e.g., 211) are optionally configured to momentarily deform in response to an electromagnetic field generated by the electrical signal in the plurality of conductive wire segments. In some embodiments, the conductive wire or trace segments optionally include one continuous wire disposed on the proximal surface of the housing. In some embodiments, the wire or trace segments optionally have one or more of the following layout shapes: serpentine (e.g., electrical current in two neighboring segments run in the opposite directions), or angular (e.g., neighboring trace segments are neither parallel nor perpendicular with each other).

In some embodiments, each conductive wire segment (e.g., 209) optionally includes a turn in the conductive wire or trace, the conductive wire or trace wound in the shape of a coil. In other words, electrical current in two neighboring wire or trace segments run in the same direction. In some embodiments each turn of the conductive coil is optionally separated from its nearest neighboring coil turn by the same distance (e.g., the conductive wire coil is wound with a constant winding density). In some embodiments, each turn in the conductive wire is optionally connected to its two neighboring wire segments. In some embodiments, the conductive wire segments are optionally formed by one continuous conductive wire or trace.

In some embodiments, the intensity is configured to cause the shock waves to dissipate in the user's scalp before the shock waves reach the user's cranium bones. In some embodiments, part of the shock wave energy generated by the shock wave device is consumed within the treated scalp skin and tissues, while the rest of the energy is substantially dissipated within the cranium bone before the wave reaches the brain. In some embodiments, the intensity is optionally between 0.001 $mJ/mm^2$ per pulse and 0.01 $mJ/mm^2$ per pulse. In some embodiments, the intensity is optionally between 0.01 $mJ/mm^2$ per pulse and 0.1 $mJ/mm^2$ per pulse. In some embodiments, the intensity is optionally between 0.1 $mJ/mm^2$ per pulse and 0.2 $mJ/mm^2$ per pulse.

In some embodiments, each corresponding shock wave optionally has an adjustable intensity. In some embodiments, a subset of the shock wave generators (e.g., 208) optionally generates corresponding shock waves that have a different intensity than the corresponding shock waves generated by the rest of the plurality of shock wave generators. In some embodiments the subset of shock wave generators optionally includes one shock wave generator. In some embodiments, the different levels of intensity are optionally achieved using the controller/power supply unit (e.g., 402). The configurable intensity of the shock waves generated offers more customizable treatment options for various indications and severities, thereby making the shock wave therapy more effective.

In some embodiments, the coupling assembly (e.g., 212) optionally includes a flexible layer configured to contact the scalp. In some embodiments, the flexible layer is optionally made from elastomers such as silicone, natural rubber, neoprene rubber, or Thermoplastic Elastomers (TPE). In some embodiments, the sac is optionally configured to cover substantially the entire proximal surface (e.g., 210). In some embodiments, the coupling assembly further includes shock wave couplant disposed between the plurality of shock wave generators and the flexible layer, the shock wave couplant configured to transmit shock waves generated by the plurality of shock wave generators to the flexible layer. In some embodiments, the shock wave couplant is optionally an aqueous gel containing polyols or other suitable types of liquids or gels generally known in the art. In some embodiments, the shock wave couplant optionally includes corrosion inhibitors. The coupling assembly with the optional flexible layer and couplant allows generated shock waves be transmitted more effectively to the scalp, thereby increasing the treatment efficacy and reducing treatment time.

In some embodiments, the extracorporeal shock wave apparatus optionally includes a control and power supply unit (e.g., 400) configured to connect electrically to the plurality of shock wave generators, the control and power supply unit configured to control the coupling assembly and a group of the plurality of shock wave generators. In some embodiments, the group of the shock wave generators is optionally a subset (including one) of the shock wave generators. In some embodiments the group of the shock wave generators is all of the shock wave generators. In some embodiments, the control and power supply unit optionally generates an electrical control signal to be sent to the shock wave generators. In some embodiments the electrical control signal is optionally a pulse voltage signal to control one or more piezoelectric ceramic tile shock wave generator. In some embodiments, the electrical control signal is optionally a pulse current signal to control a conductive wire segment shock wave generator. In some embodiments, the control and power supply unit optionally includes one or more user-selectable settings that adjust the intensity of shock wave pressure pulses produced by a group of the shock wave generators by, for example, adjusting a magnitude or a phase of the pulse voltage signal or the pulse current signal. In some embodiments the control and power supply unit optionally controls the inflation and deflation of the deformable sac in the coupling assembly by filling the deformable sac with shock wave transmission fluid or draining shock wave transmission fluid from the deformable sac. In some embodiments, the control and power supply unit optionally includes one or more user-selectable settings that adjust the amount of shock wave transmission fluids in the sac. In some embodiments, the control and power supply unit optionally receives an electrical signal corresponding to a measured pressure value from the coupling unit and, in accordance with the measure pressure, stops filling the sac with shock wave transmission liquid. The control unit improves usability of the shock wave device by providing easy ways to adjust the intensity of generated shock waves and the coupling between the shock wave device and the scalp being treated, thereby making the shock wave therapy more effective.

Figure 5B:
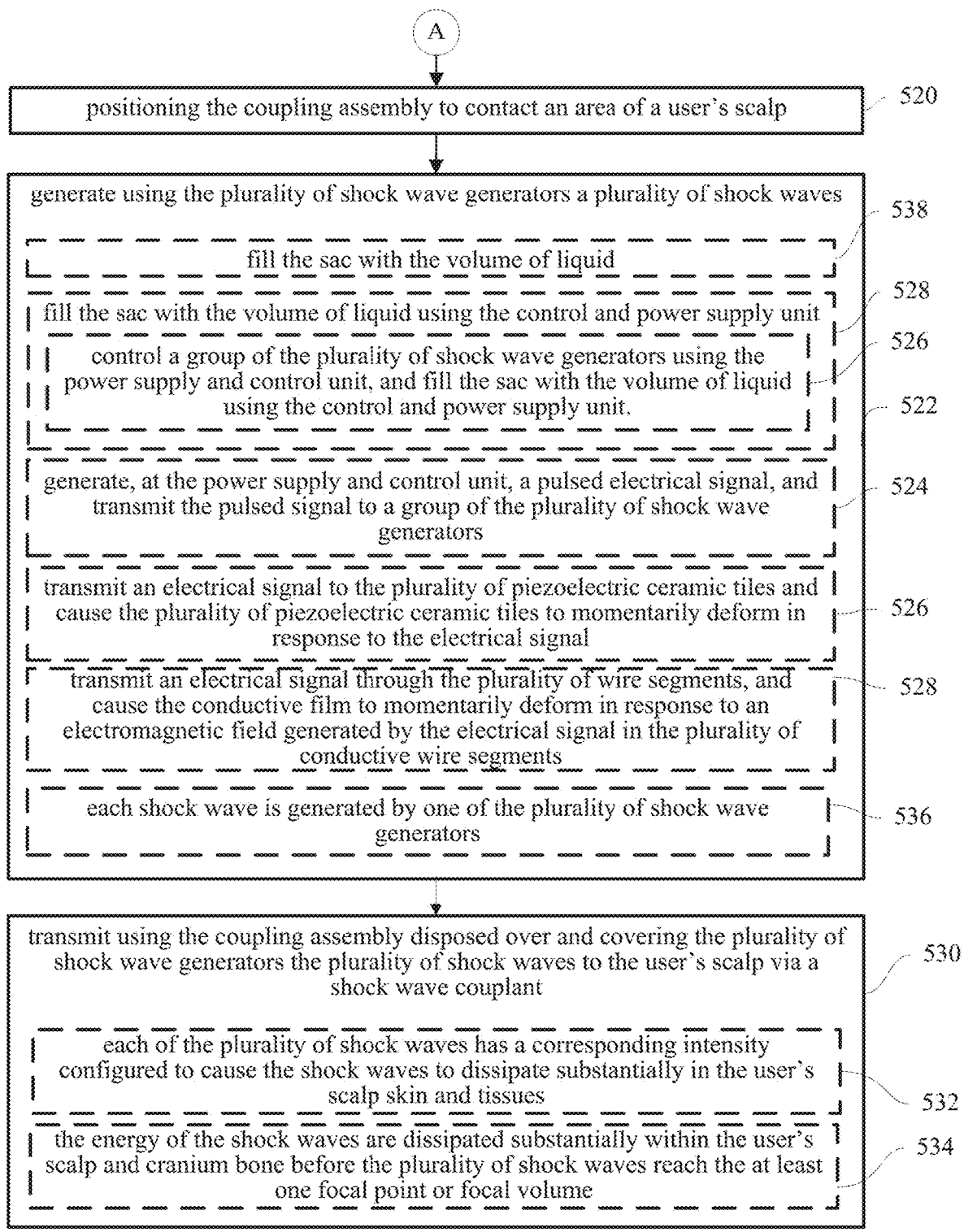

FIGS. 5A-5B illustrate methods of using a shock wave device according to various aspects of the present disclosure. In some embodiments, the method includes (e.g., step 502) using an extracorporeal shock wave apparatus (e.g., 200) that includes a housing (e.g., 202), a plurality of shock wave generators (e.g., 208) disposed on a first surface (e.g., 210) of the housing (e.g., 202), and a coupling assembly (e.g., 212) disposed over and covering the plurality of shock wave generators such that the plurality of shock wave generators (e.g., 208) are sandwiched by the housing (e.g., 202) and the coupling assembly (e.g., 212), the method includes: position the coupling assembly (e.g., 212) to contact an area of a user's scalp (e.g., step 520); generate, using the plurality of shock wave generators (e.g., 208), a plurality of shock waves (e.g., step 522), such that each shock wave is generated by one of the plurality of shock wave generators; and transmit, using the coupling assembly disposed over and covering the plurality of shock wave generators, the plurality of shock wave to the user's scalp via a shock wave couplant (e.g., step 530), where each of the plurality of shock waves is generated by one of the plurality of shock wave generators (e.g., step 536). In some embodiments, each of the plurality of shock waves has a corresponding intensity configured to cause the shock waves to dissipate substantially in the user's scalp skin and tissues (e.g., step 532).

In some embodiments, (e.g., step 504), the first surface (e.g., proximal surface 210) is not convex and has at least one geometric real focal point or focal volume, and the coupling assembly (e.g., 212) is configured to transmit the plurality of shock waves to the user's scalp such that the energy of the shock waves are dissipated substantially within the user's scalp and cranium bone before the plurality of shock waves reach the at least one focal point or focal volume (e.g., step 534).

In some embodiments, the shock wave generators disclosed in step optionally includes (e.g., step 510) a plurality of piezoelectric ceramic tiles (e.g., 208), and the method optionally includes transmitting an electrical signal to the plurality of piezoelectric ceramic tiles (e.g., step 510) and the method optionally includes causing the plurality of piezoelectric ceramic tiles to momentarily deform in response to the electrical signal (e.g., step 526). In some embodiments, the shock wave generators optionally include (e.g., step 514) a plurality of conductive wire segments (e.g., a turn in the conductive wire wound in the shape of a coil (e.g., 209)) sandwiching the first surface (e.g., 210) of the housing and a conductive film (e.g., 211), and the method optionally includes transmitting an electrical signal through the conductive wire segments and causing a momentary deformation in the conductive film in response to the electromagnetic field generated by the electrical signal in the conductive wire segments (e.g., step 528).

In some embodiments, the coupling assembly optionally includes a flexible layer sandwiching a couplant with the plurality of shock wave generators (e.g., step 512). In some embodiments, the coupling assembly optionally includes (e.g., step 516) a sac (e.g., 218) configured to contain a volume of liquid, and the method optionally includes filling the sac with a volume of liquid (e.g., step 538).

In some embodiments, the shock wave apparatus (e.g., 200) optionally includes a control and power supply unit (e.g., 402) configured to connect electrically to the plurality of shock wave generators and the method optionally includes controlling a group of the plurality of shock wave generators (e.g., e.g., 208) using the power supply and control unit (e.g., step 526). In some embodiments, the method optionally includes filling the sac with the volume of liquid using the control and power supply unit (e.g., step 526). In some embodiments, controlling a group of the plurality of shock wave generators using the power supply and control unit optionally includes the steps of generating, at the power supply and control unit (e.g., 400), a pulsed electrical signal and transmitting the pulsed signal to a group of the plurality of shock wave generators (step 524).

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. A method for applying treatment to a user's scalp, comprising:
    positioning a coupling assembly of an extracorporeal shock wave apparatus to contact an area of the user's scalp, wherein the coupling assembly comprises shock wave couplant and a deformable sac configured to be in contact with the area of the user's scalp;
    generating, using a plurality of shock wave generators of the extracorporeal shock wave apparatus, a plurality of shock waves,
        wherein the plurality of shock wave generators are disposed on a first surface of a housing of the extracorporeal shock wave apparatus and are sandwiched by the coupling assembly and the first surface,
        wherein the first surface of the housing is flat or concave in the same direction as the user's scalp, and
        wherein the plurality of shock wave generators are in contact with the shock wave couplant of the coupling assembly; and
    transmitting, using the coupling assembly disposed over and covering the plurality of shock wave generators, the plurality of shock waves to the user's scalp via the shock wave couplant.

2. The method in claim 1, wherein the first surface has at least one geometric real focal point or focal volume, and the coupling assembly is configured to transmit the plurality of shock waves to the user's scalp before the plurality of shock waves reach the at least one focal point.

3. The method in claim 1, wherein the plurality of shock wave generators comprising a plurality of piezoelectric ceramic tiles, the method further comprising:
    transmitting an electrical signal to the plurality of piezoelectric ceramic tiles; and
    causing the plurality of piezoelectric ceramic tiles to momentarily deform in response to the electrical signal.

4. The method in claim 1, wherein the plurality of shock wave generators comprising a plurality of conductive wire segments sandwiching the first surface of the housing and a conductive film, the method further comprising:
    transmitting an electrical signal through the plurality of wire segments; and
    causing the conductive film to momentarily deform in response to an electromagnetic field generated by the electrical signal in the plurality of conductive wire segments.

5. The method in claim 1, wherein the coupling assembly further comprises a flexible layer configured to contact the scalp.

6. The method in claim 1, wherein the deformable sac is configured to contain a volume of liquid, the method further comprising: filling the sac with a volume of liquid.

7. The method in claim 6, wherein the apparatus further comprising a control and power supply unit configured to connect electrically to the plurality of shock wave generators, the method further comprising:
 controlling a group of the plurality of shock wave generators using the power supply and control unit; and
 filling the sac with the volume of liquid using the control and power supply unit.

8. The method in claim 7, wherein controlling a group of the plurality of shock wave generators using the power supply and control unit further comprising:
 generating, at the power supply and control unit, a pulsed electrical signal; and
 transmitting the pulsed signal to a group of the plurality of shock wave generators.

* * * * *